United States Patent [19]

Yamashita et al.

[11] 4,140,364
[45] Feb. 20, 1979

[54] VARIABLE FIELD OPTICAL SYSTEM FOR ENDOSCOPES

[75] Inventors: Nobuo Yamashita, Tama; Katsuyuki Kanehira, Hachiouji, both of Japan

[73] Assignee: Olympus Optical Co., Ltd., Tokyo, Japan

[21] Appl. No.: 857,991

[22] Filed: Dec. 5, 1977

Related U.S. Application Data

[63] Continuation of Ser. No. 649,519, Jan. 15, 1976, abandoned, which is a continuation of Ser. No. 482,030, Jun. 21, 1974, abandoned.

[30] Foreign Application Priority Data

Jun. 23, 1973 [JP] Japan .................................. 48-74067

[51] Int. Cl.$^2$ ............................................. G02B 23/02
[52] U.S. Cl. ..................................................... 350/26
[58] Field of Search .................... 350/96.26, 21–26, 350/52, 48; 354/62, 63

[56] References Cited

U.S. PATENT DOCUMENTS

| | | | |
|---|---|---|---|
| 1,530,081 | 3/1925 | Humbrecht et al. | 350/26 |
| 2,817,994 | 12/1957 | Ehrenhaft et al. | 350/26 |
| 3,856,000 | 12/1974 | Chikama | 350/96.26 |
| 3,918,072 | 11/1975 | Imai et al. | 350/96.26 |

*Primary Examiner*—Jon W. Henry
*Attorney, Agent, or Firm*—Cushman, Darby & Cushman

[57] ABSTRACT

A variable field optical system for endoscopes comprising an image guide, objective, fixed prism and rotatable prism and enabling to observe over a wide range by varying the field by rotating said rotatable prism.

5 Claims, 9 Drawing Figures

VARIABLE FIELD OPTICAL SYSTEM FOR ENDOSCOPES

This is a continuation, of application Ser. No. 649,519 filed Jan. 15, 1976 now abandoned which was a continuation of Ser. No. 482,030 filed June 21, 1974 now abandoned.

BACKGROUND OF THE INVENTION (a) Field of the Invention

The present invention relates to an optical system of endoscopes having flexible optical fiber and used for observing the inside of body cavities or inside of tubes in industrial field.

(b) Description of the Prior Art

For example, endoscopes now available for medical purposes for observing the inside of a stomach, esophagus, etc. can be classified into two typical types. One is the forward-viewing type for observing along the axis of the distal end of the endoscope and the other is the side-viewing type for observation in a direction at a right angle to the axis of the distal end. These two types have advantages and disadvantages respectively. For example, in a narrow tubular portion such as the esophagus, it is sometimes very difficult to use the side-viewing type endoscope because the sight for observation becomes narrow and, moreover, it is difficult to provide a sufficient optical length because the distance between the lens and object is short. By the forward-viewing type endoscope, it is possible to observe from comparatively distant positions to near positions. Therefore, in such narrow tubular portions, forward-viewing type endoscopes are generally used. On the other hand, in a wide baglike cavity such as a stomach, side-viewing type endoscopes are generally used because it is possible to observe all over the side walls. For such reasons, side-viewing endoscopes and forward-viewing type endoscopes are used for different applications according to characteristics of the portion to be observed so that their advantages can be fully utilized. When, however, it is required for example to observe the esophagus and stomach of one patient at the same time, it is necessary to use two endoscopes successively for the above reason. This is very inconvenient and, moreover, pain of the patient is extremely large. To solve the above problems, endoscopes which can be used for both of side-viewing and forward-viewing are provided. One example of such endoscopes is shown in FIG. 1. In this example, a mirror 1 is arranged at the end of an endoscope and it is arranged to carry out side-viewing as shown by the full line and forward-viewing as shown by the dotted line by inserting and removing the mirror 1. FIG. 2 shows another example of such endoscope in which it is arranged to continuously rotate the mirror 1. The former example, however, has a disadvantage that the image becomes upside down. That is, the image rotates. The latter example has advantages that the image does not become upside down and that the observing direction can be changed continuously. However, by the latter example, perfect forward-viewing is impossible and, moreover, the endoscope itself has to be made large.

SUMMARY OF THE INVENTION

It is, therefore, a primary object of the present invention to provide a variable field optical system for endoscopes having two prisms at the end of an endoscope and arranged to change the field by rotating one of said prisms.

Another object of the present invention is to provide a variable field optical system for endoscopes for which the length of the optical system is made shorter by arranging lens components of the objective close to the incident surface and emerging surface of the fixed prism respectively.

Still another object of the present invention is to provide a variable field optical system for endoscopes arranged so that the emerging surface of the fixed prism will refract the emerging ray.

DETAILED DESCRIPTION OF THE PREFERRED EMBODIMENTS

Figure 1:
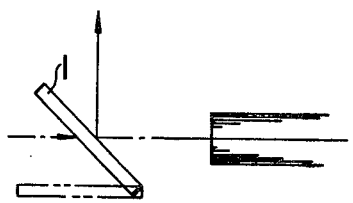
FIG. 1 and FIG. 2 respectively show conventional variable field optical system for endoscopes.
Figure 2:
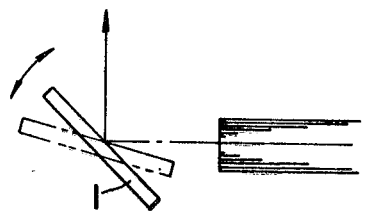
Figure 3:
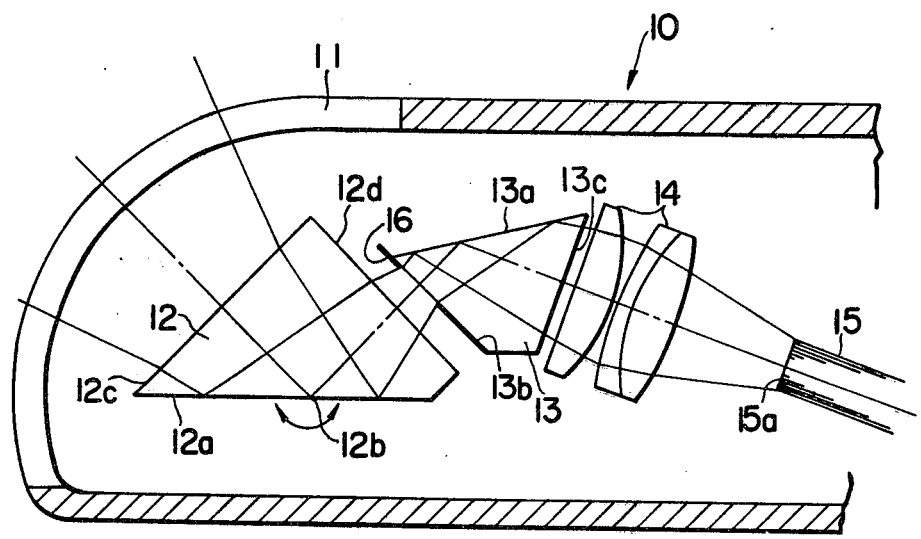
FIG. 3 shows an embodiment of the variable field optical system according to the present invention.
Figure 4A:
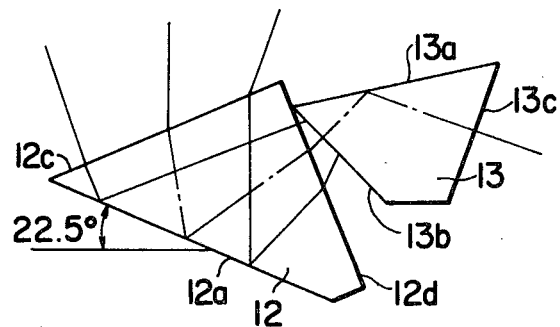
FIG. 4A shows the case when the optical system according to the present invention is used for side-viewing.
Figure 4B:
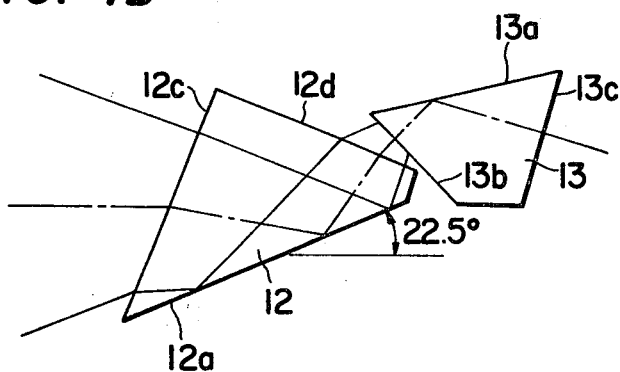
FIG. 4B shows the case when the optical system according to the present invention is used for forward-viewing.

In the following, the concrete contents of the optical system according to the present invention are described in detail referring to the accompanying drawings. In FIG. 3, numeral 10 designates a distal end of an endoscope, numeral 11 designates a cover glass, numeral 12 designates a rotatable prism, numeral 13 designates a fixed prism, numeral 14 designates an objective, numeral 15 designates an image fiber and numeral 16 designates an aperture stop. In the above, the rotatable prism 12 is an isosceles right triangular prism of 45° and is arranged rotatable around the center position 12b of its surface 12a in the rotating direction shown by arrowheads in the figure. In the above-mentioned optical system, the ray from the object to be observed comes in through the cover glass 11, is totally reflected by the surface 12a of the rotatable prism 12 and is totally reflected again by the surface 13a of the fixed prism 13. After the above, the ray from the object is imaged on the end face 15a of the image fiber 15 by the objective 14. The arrangement shown in FIG. 3 is for the case of observing in the aslant direction of 45° from the forward-viewing direction. It is, however, evident that the observing direction can be changed continuously when the rotatable prism 12 is rotated around its axis of rotation 12b. FIG. 4A and FIG. 4B respectively show those cases when the rotatable prism is positioned for side-viewing direction and forward-viewing direction respectively by rotating said rotatable prism 12. That is, when the rotatable prism 12 is rotated so that its surface 12a is inclined in clockwise direction by 22.5° from the horizontal direction as shown in FIG. 4A, the ray from the object becomes incident to the surface 12c from above to enable side-viewing. When the rotatable prism 12 is rotated so that its surface 12a is inclined in counterclockwise direction by 22.5° as shown in FIG. 2B, the ray from the object becomes incident to the surface 12c from horizontal direction to enable forward-viewing. The fixed prism 13 is arranged so that the optical axis becomes always vertical to the incident surface 13b and emerging surface 13c of the prism 13. Besides, the rotatable prism 12 and fixed prism 13 are so arranged that the extension line from the optical axis incident to the fixed prism 13 (extended in the direction opposite to the direction of incidence in the figure) will always intersect with the axis of rotation of the rotatable prism 12.

Figure 5:
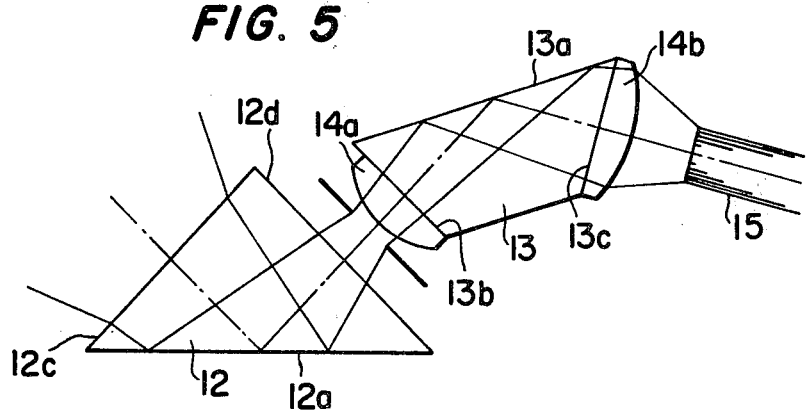
FIG. 5 and FIG. 6 respectively show other embodiments of the optical system according to the present invention.

FIG. 5 shows another embodiment of the optical system according to the present invention in which the objective 14 is so arranged that the lens components 14a and 14b of said objective 14 are positioned on both sides of the fixed prism 13. In this embodiment, two lens components 14a and 14b can be arranged to closely contact the fixed prism 13.

Figure 6:
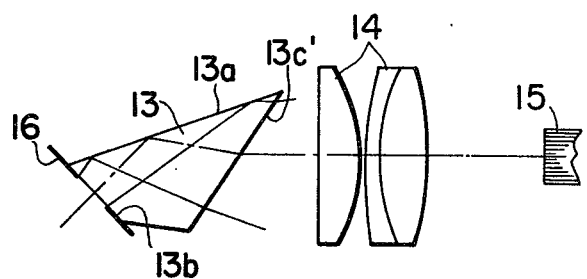

FIG. 6 shows still another embodiment of the optical system according to the present invention. In this embodiment, the shape of the fixed prism 13 is varied so that the ray will be refracted by the emerging surface 13c' of the prism 13. That is, the emerging surface 13c' is arranged not vertical to the optical axis but inclined in respect to the optical axis. Therefore, as it is evident from FIG. 3 and FIG. 5, it is necessary for the former two embodiments to incline the end of the image fiber on the objective side in slightly upward direction. In the last embodiment shown in FIG. 6, however, it is not necessary to incline said end of the image fiber.

Figure 7:
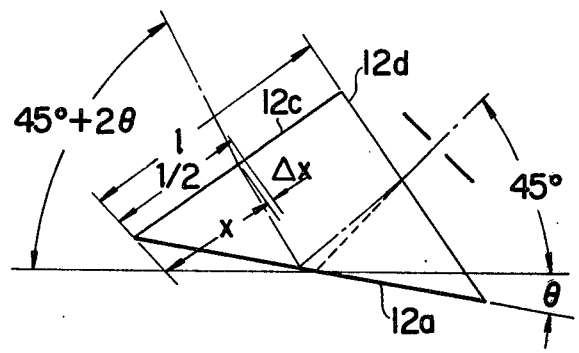
FIG. 7 shows an explanatory figure for illustrating the amount of displacement of the optical axis in relation to the rotating angle of the rotatable prism in the optical system according to the present invention.

Now, let us consider on change of the incident position of optical axis to the incident surface 12c of the rotatable prism 12 when the observing direction is changed by rotating the rotatable prism 12 of the optical system according to the present invention. When the length of one side of the surface 12c of the rotatable prism 12 in FIG. 7 is represented by reference symbol l, the incident position of the optical axis when the rotatable prism is rotated by the angle $\theta$ is represented by reference symbol x, and the amount of displacement of the principal ray from the central position is represented by reference symbol $\Delta x$, x and $\Delta x$ can be expressed by the following equations.

$$x = \frac{1}{2} l(1 - \tan\theta + \frac{2\sin\theta}{n})$$

$$\Delta x = x - \frac{1}{2} l = \frac{1}{2} l(\frac{2\sin\theta}{n} - \tan\theta)$$

Figure 8:
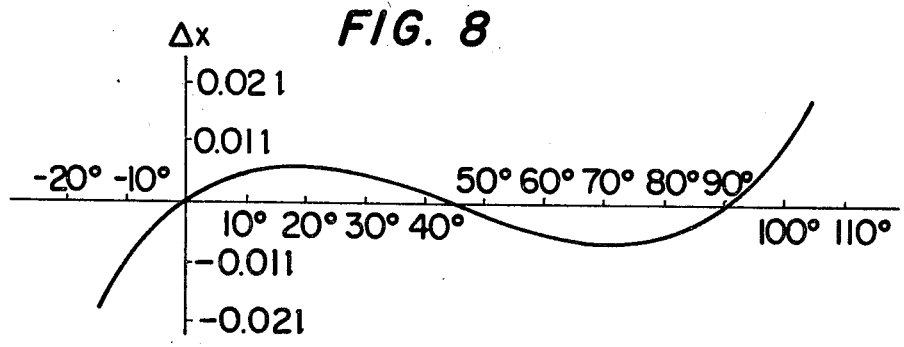
FIG. 8 shows a graph illustrating the relation between said rotating angle and amount of displacement of the optical axis.

FIG. 8 shows a graph illustrating values of displacement $\Delta x$ of the incident position in relation to $\theta$ based on the above equations. This figure shows the case when the refractive index of the prism is 1.84776. In this graph, the abscissa represents the value of 45° + 2$\theta$ and the ordinate represents $\Delta x$. As it is evident from this figure, the amount of displacement of the incident position over the range from the side-viewing position, i.e., 90° (where $\theta = 22.5°$) to the forward-viewing position, i.e., 0° (where $\theta = -22.5°$) is only a very small value.

As it is described in the above, the variable field optical system for endoscopes according to the present invention has a very simple construction in which the rotatable prism and fixed prism are arranged in combination, but this optical system realizes extremely favourable observation over a wide range from side-viewing direction to forward-viewing direction without causing such problems as rotation of the image. Moreover, as surfaces of total reflection of prisms are utilized as reflecting surfaces, large reflecting surfaces are not required because of refraction of prisms. Besides, as shown in FIG. 8, the displacement of positions of the optical axis at the incident and reflecting surfaces of the rotary prism when the observing direction is varied is extremely small. Therefore, each element of the optical system can be made very small. Besides, as described before, the fixed prism is so arranged that the extension line from the optical axis incident to the fixed prism always intersects with the axis of rotation of the rotatable prism. Consequently, very favourable observation becomes possible when the optical system according to the present invention is used.

We claim:

1. A variable field optical system for endoscopes capable of varying the field at a distal end of an endoscope and comprising a curved cover glass provided at the distal end, a rotatable prism having a single planar reflecting surface opposed to an object through said cover glass and rotatable round an axis of rotation included in the plane including said planar reflecting surface and positioned at about the middle of said reflecting surface so that said axis of rotation intersects the optical axis of said optical system at a right angle, a fixed prism having incident and emerging surfaces and a single planar reflecting surface whereon the ray from said rotatable prism is incident and is reflected, an aperture stop arranged between said rotatable prism and said fixed prism, and an objective for focusing an image of the ray from said fixed prism on one end face of an image guide, said variable field optical system for endoscopes being capable of varying the observing field continuously from the forward-viewing direction to the side-viewing direction by rotating said rotatable prism round said axis of rotation.

2. A variable field optical system for endoscopes according to the claim 1 in which both of the incident and emerging surfaces of said fixed prism are arranged perpendicular to the optical axis of said optical system.

3. A variable field optical system for endoscopes according to the claim 1 in which said fixed prism and rotatable prism are arranged so that the extension line from the optical axis incident to said fixed prism intersects with the axis of rotation of said rotatable prism.

4. A variable field optical system for endoscopes according to the claim 1 in which said objective is arranged so that respective lens components of said objective closely contact the incident surface and emerging surface of said fixed prism respectively.

5. A variable field optical system for endoscopes according to the claim 1 in which the emerging surface of said fixed prism is arranged to refract the emerging ray.

* * * * *